(12) United States Patent
Shen et al.

(10) Patent No.: US 8,322,227 B2
(45) Date of Patent: Dec. 4, 2012

(54) TENSION TESTING DEVICE

(75) Inventors: Xin Shen, Wujiang (CN); Wenxiang Ou, Wujiang (CN); Ching-Feng Hsieh, Taipei (TW)

(73) Assignee: Askey Computer Corp. (TW)

( * ) Notice: Subject to any disclaimer, the term of this patent is extended or adjusted under 35 U.S.C. 154(b) by 77 days.

(21) Appl. No.: 13/111,352

(22) Filed: May 19, 2011

(65) Prior Publication Data

US 2012/0247221 A1    Oct. 4, 2012

(30) Foreign Application Priority Data

Apr. 1, 2011   (TW) .............................. 100111540 A (51) Int. Cl.
*G01N 3/08*   (2006.01)
(52) U.S. Cl. ......................................................... 73/827
(58) Field of Classification Search ...................... 73/827
See application file for complete search history.

(56) References Cited

U.S. PATENT DOCUMENTS

| | | | | |
|---|---|---|---|---|
| 2,687,642 A | * | 8/1954 | Livermont | 73/862.639 |
| 2,968,179 A | * | 1/1961 | Scarvelis | 73/795 |
| 3,580,065 A | * | 5/1971 | Strittmater et al. | 73/150 R |
| 4,263,811 A | * | 4/1981 | Shaw | 374/50 |
| 4,893,513 A | * | 1/1990 | Schroeder et al. | 73/827 |

* cited by examiner

*Primary Examiner* — Lisa Caputo
*Assistant Examiner* — Octavia Davis-Hollington
(74) *Attorney, Agent, or Firm* — Schmeiser, Olsen & Watts, LLP (57) ABSTRACT

A tension testing device for use in a tension test for evaluating the strength of bond between a body and a pin of an electronic device includes a base, a tensiometer, a hanger, and a clamp. The base includes a supporting member and a carrying member, wherein the tensiometer is carried by the carrying member and includes a pulling portion. The hanger is coupled to the pulling portion for underpinning the body and project the pin in the direction of the base. The clamp is disposed on the base, positioned beside the hanger, for clamping the pin. The tension testing device protects the electronic device against test-induced deformation, dispenses with an intricate step of the welding and unwelding of the pin and a test lead, precludes a tension test-induced component of force, manifests ease of use, ensures test stability, and enhances test efficiency and reliability.

10 Claims, 6 Drawing Sheets

TENSION TESTING DEVICE

CROSS-REFERENCE TO RELATED APPLICATION

This non-provisional application claims priority under 35 U.S.C. §119(a) on Patent Application No(s). 100111540 filed in Taiwan, R.O.C. on Apr. 1, 2011, the entire contents of which are hereby incorporated by reference.

FIELD OF TECHNOLOGY

The present invention relates to tension testing devices, and more particularly, to a tension testing device for use with a tension test for evaluating a bonding strength between a body and a pin of an electronic element.

BACKGROUND

An electronic element in wide use usually has a body and a pin (also known as a lead, an outlet, a guide, a negative/positive terminal, and a negative/positive lead wire) connected to the body. Electronic elements of this kind include, but are not limited to, resistors, capacitors, inductors, diodes, and transistors. The pin is electrically connected to the body of the electronic element and a circuit board. The strength of the bonding between the body and the pin of the electronic element is a factor in the stability of electrical connection of the circuit board and therefore is a factor in the use and quality of electronic products. Hence, manufacturing processes of various electronic elements entail conducting a pin strength tension test thereon to make sure that the electronic elements thus manufactured meet product requirements and verification standards—for example, even when subjected to a specific tension, the body and the pin of the electronic element do not separate, nor does the pin sever.

The bonding strength between the body and the pin of the electronic element depends on the process flow of a manufacturing process thereof. Take an electrolytic capacitor as an example, the manufacturing process thereof comprises: (1) a nailing step: coupling an anode foil and the pin, followed by coupling a cathode foil and the pin, both by nailing or riveting, to form a positive pin and a negative pin which are exposed from the body of the electrolytic capacitor; (2) a winding step: positioning an electrolytic paper between the anode foil and the cathode foil, wherein the electrolytic paper is wound and fixed in place; (3) an immersing step: the electrolytic paper absorbs an electrolyte so as to form a dielectric disposed between an anode and a cathode; (4) an assembling and sealing step: covering the electrolytic capacitor with an aluminum casing, mounting a rubber lid thereon, protruding the pin out of the rubber lid, and hermetically sealing the electrolytic capacitor with a plastic film; and (5) a pin-cutting and tape-affixing processing step. The nailing step, the winding step, and the assembling and sealing step are the crucial steps in determining the bonding strength between the body and the pin of the electrolytic capacitor. Hence, it is necessary to perform a pin strength tension test so as to ensure that the electronic element will meet product requirements and verification standards.

Figure 1:
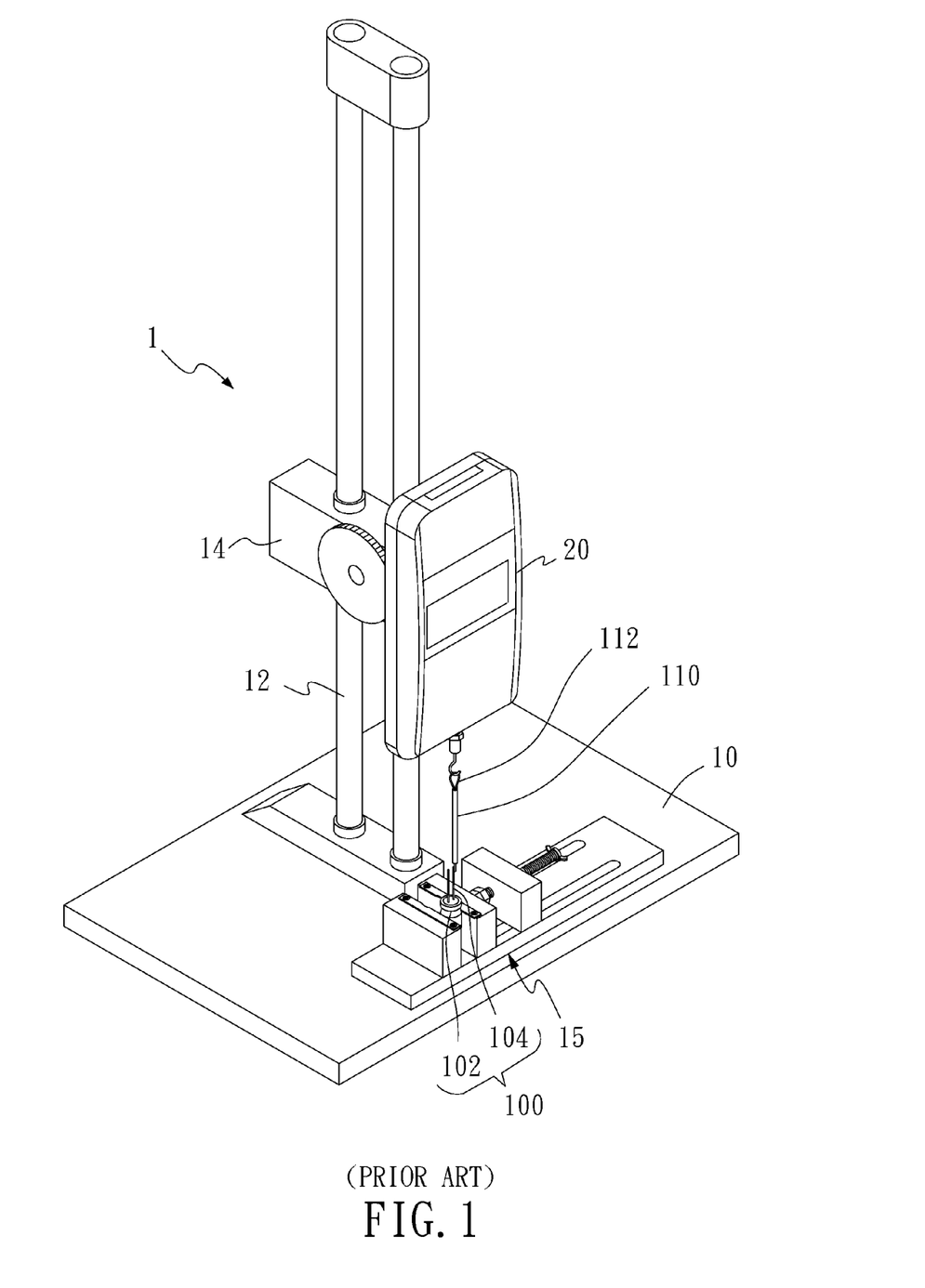
FIG. 1 (PRIOR ART) is a schematic view of a conventional tension testing device.

Referring to FIG. 1, there is shown a schematic view of a conventional tension testing device for use with a pin strength tension test. As shown in FIG. 1, a tension testing device 1 comprises a base 10, a supporting member 12, a carrying member 14, a tensiometer 20, and a clamp 15. The tension testing device 1 is for performing a tension test on a body 102 and a pin 104 of an electronic element 100 to evaluate the bonding strength between the body 102 and the pin 104. The supporting member 12 is fixed in position on the base 10 and provided with the carrying member 14 whose position is adjustable. The carrying member 14 is for carrying the tensiometer 20 and adjusting the height of the tensiometer 20. The clamp 15 is for clamping the body 102 in a manner that the pin 104 points at the tensiometer 20 so as for the tension test to be conducted. When performed by means of the tension testing device 1, the tension test comprises the steps of: (1) welding the pin 104 and a test lead 110 together, wherein a hook portion 112 is formed at the other end of the test lead 110; (2) hanging the hook portion 112 of the test lead 110 at the tensiometer 20, followed by clamping the body 102 with the clamp 15; (3) starting the tensiometer 20, setting a preset tension level and a duration of continuity thereof, and performing the tension test; and (4) unwelding the pin 104 and the test lead 110 as soon as the tension test is done.

However, according to the prior art, it is necessary to weld the pin 104 and the test lead 110 together before performing a tension test with the conventional tension testing device 1. The welding process causes thermal stress to develop in the pin 104 to the detriment of the material strength of the pin 104. Also, external stress is produced in the step of clamping the body 102 with the clamp 15, thereby deforming the body 102 to the detriment of its appearance and even its internal structure. Furthermore, the step of clamping the body 102 with the clamp 15 is not quantified in terms of a clamping force and position, thereby resulting in a lack of consistency of a parameter in a plurality of instances of the tension test and therefore a negative effect on the accuracy of the result of the tension test. Also, the welding process performed on the test lead 110 contributes to a component of force derived from the applied tension, thereby deforming or bending the pin 104; with the deformed or bent pin 104 being no longer vertical, no tension can be fully applied to the electronic element 100. Last but not least, the step of hanging the hook portion 112 of the test lead 110 at the tensiometer 20 has a drawback: unless the body 102, the pin 104, the test lead 110, and the hook portion 112 are aligned, a component of force which is not vertical will derive from the applied tension.

In conclusion, a conventional tension testing device is likely to compromise the appearance of an electronic element under test, create a force component derived from an applied tension to thereby affect the tension test result, and render the tension test complicated, inconvenient, and inefficient. Accordingly, it is imperative to provide a pin tension testing device that features ease of use, enhances the stability of a test procedure, and yields a reliable tension test result, thereby enhancing the efficiency of production and the quality of products.

SUMMARY

It is an objective of the present invention to provide a tension testing device that enables a pin tension test to be performed on an electronic element conveniently and quickly, prevents the electronic element under test from being damaged as a result of a welding process or a clamping process, stabilizes the tension test process, and enhances the reliability of the tension test result.

In order to achieve the above and other objectives, the present invention provides a tension testing device for use with a tension test for evaluating a bonding strength between a body and a pin of an electronic element. The tension testing device comprises: a base provided thereon with a supporting member and provided with a carrying member disposed at the supporting member; a tensiometer carried by the carrying member and having a pulling portion; a hanger coupled to the pulling portion for underpinning the body and project the pin in the direction of the base; and a clamp disposed on the base, positioned beside the hanger, for clamping the pin.

Unlike a conventional tension testing device, the tension testing device of the present invention simplifies a testing procedure, enhances ease of use, shortens the required duration of a tension test, and enhances the efficiency of the tension test. A pin strength tension test conducted on an electronic element by the tension testing device of the present invention has the following advantages: preventing the body from being clamped to deformation or bad alignment; dispensing a welding and unwelding process which must otherwise be performed on a pin and a test lead to the detriment of the appearance of the electronic element according to the prior art; with a hanger and a clamp working together, the development of a force component derived from an applied tension is precluded, thereby providing a stable test process and yielding a reliable test result. Accordingly, the tension testing device of the present invention features ease of use, a stable test process, and reliable test results, and is effective in enhancing production efficiency and product quality.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION

Figure 2:
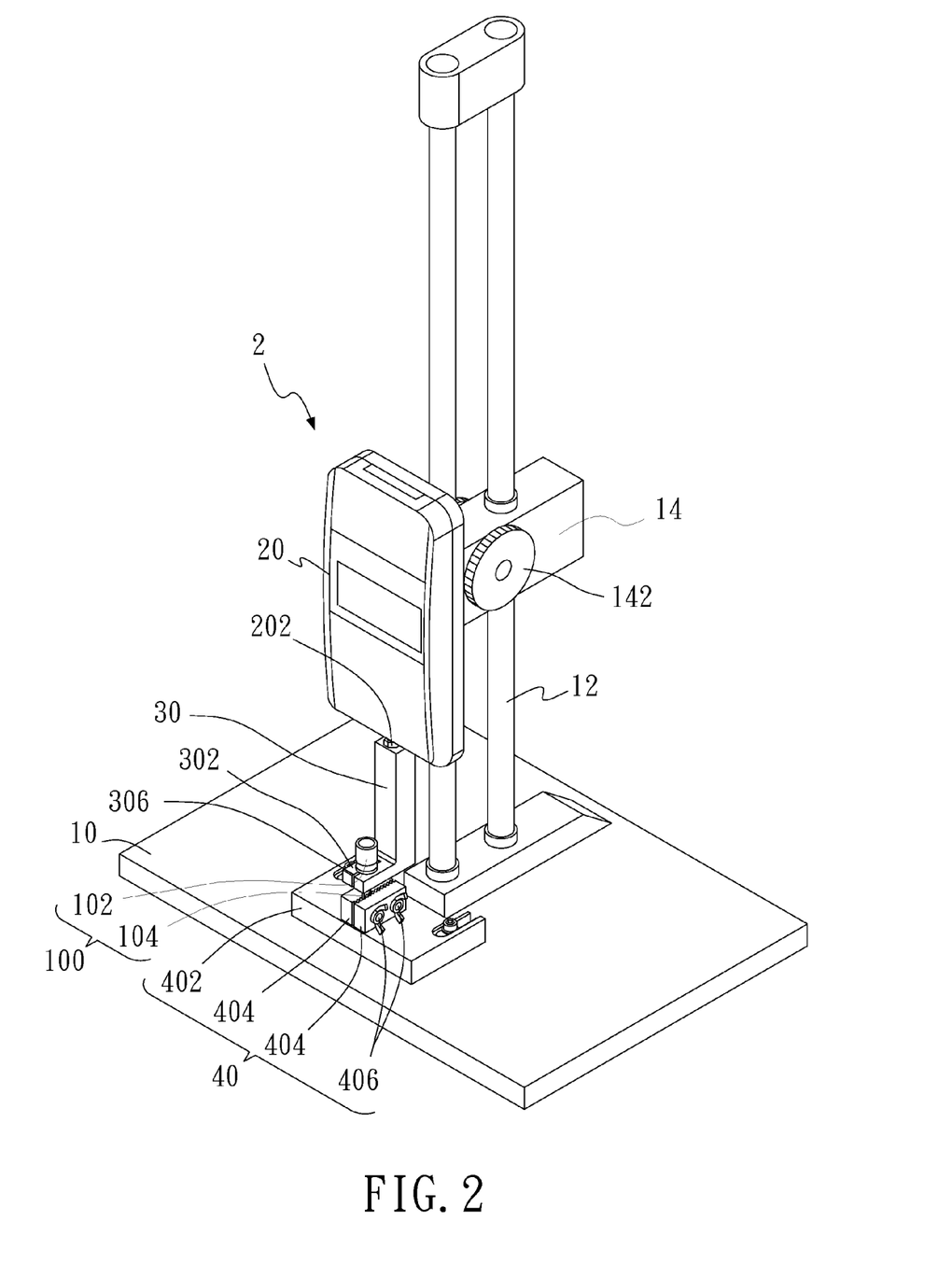
FIG. 2 is a perspective view of a tension testing device according to an embodiment of the present invention.
Figure 3:
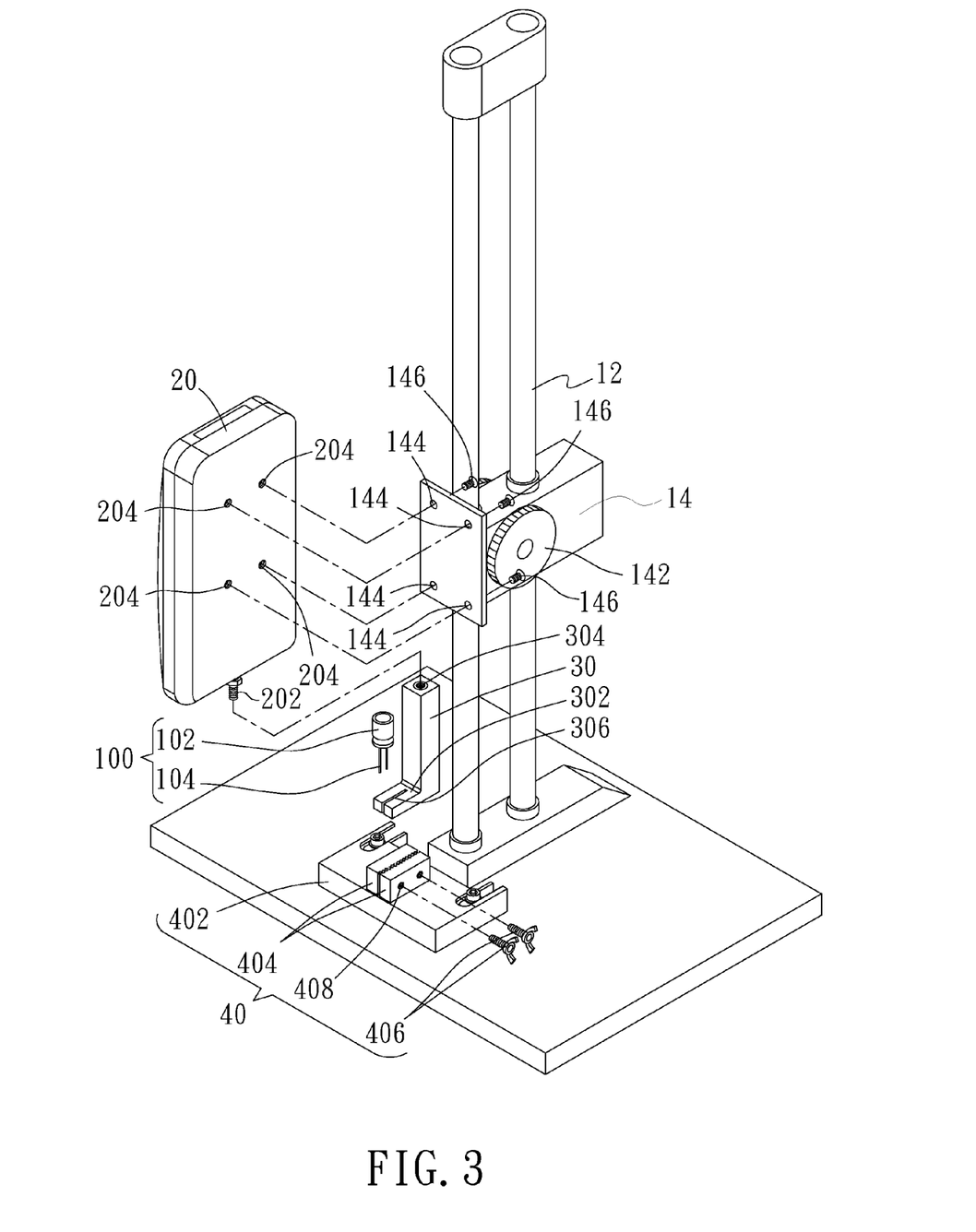
FIG. 3 is an exploded view of the tension testing device shown in FIG. 2.

Referring to FIG. 2, there is shown a perspective view of a tension testing device 2 according to an embodiment of the present invention. The tension testing device 2 is for use with a tension test which is performed on an electronic element 100 to evaluate the bonding strength between a body 102 and a pin 104 of the electronic element 100. As shown in FIG. 2, the tension testing device 2 comprises a base 10, a tensiometer 20, a hanger 30, and a clamp 40. The base 10 is provided thereon with a supporting member 12 and provided with a carrying member 14 disposed at the supporting member 12. The tensiometer 20 is carried by the carrying member 14 and has a pulling portion 202. The hanger 30 is coupled to the pulling portion 202 for underpinning the body 102 and project the pin 104 in the direction of the base 10. The clamp 40 is disposed on the base 10, positioned beside the hanger 30, for clamping the pin 104. The carrying member 14 comprises an adjusting mechanism 142 for adjusting the position and the height of the tensiometer 20 carried by the carrying member 14. Referring to FIG. 3 as well, at least one screw hole 204 is disposed on the back of the tensiometer 20, and at least one through hole 144 is disposed at the carrying member 14. The quantity of the through holes 144 equals the quantity of the screw holes 204. The tensiometer 20 is fixed to the carrying member 14 by the at least one screw 146 that engages with the screw hole 204 and the through hole 144 concurrently. The pulling portion 202 of the tensiometer 20 is a bolt, a ring, or a hook, and is coupled to the hanger 30.

Figure 4A:
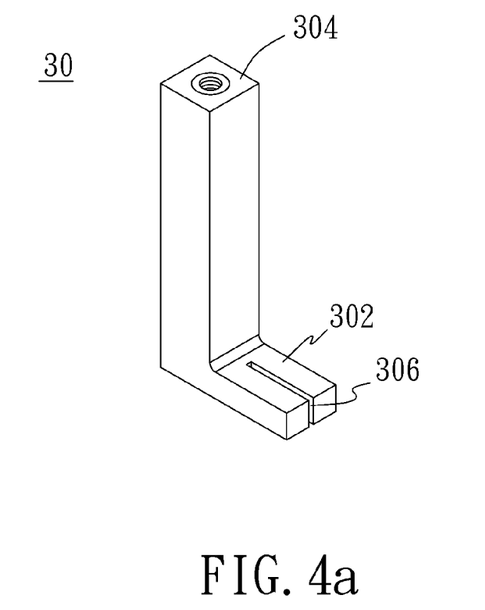
FIGS. 4a-4d are schematic views of the structure of a hanger of the tension testing device according to an embodiment of the present invention.

Referring to FIG. 2 and FIG. 4a, FIG. 4a is a schematic view of the structure of the hanger 30 shown in FIG. 2 according to an embodiment of the present invention. As shown in FIG. 4a, the hanger 30 is of an L-shaped structure and comprises a seating portion 302 and a jointing portion 304. The seating portion 302 supports the body 102 from below. The seating portion 302 has an opening 306 through which the pin 104 passes to penetrate the seating portion 302, such that the hanger 30 underpins the body 102 and projects the pin 104 in the direction of the base 10. The jointing portion 304 is located at the top end of the L-shaped hanger 30 and coupled to the pulling portion 202 of the tensiometer 20, such that the hanger 30 is hung by its own weight, that is, under gravity. The jointing portion 304 is a screw hole, a ring, or a hook. With the L-shaped hanger 30 being hung under gravity, the tension is applied vertically to the body 102 to thereby preclude a force component when the pin 104 is being stretched. Even if the included angle of the L-shaped hanger 30 per se is not a right angle because of a manufacturing tolerance, the tension test can be preceded by a pre-test procedure that involves measuring the hanger 30, calibrating the measurements, and calculating a force component, so as to analyze the tension test result accurately.

Figure 5A:
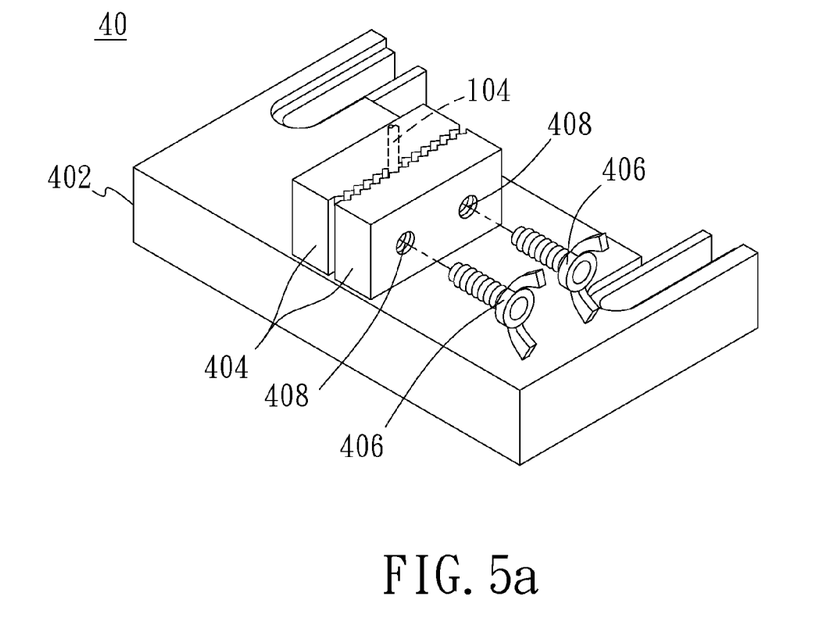
FIGS. 5a-5b are schematic views of the structure of a clamp of the tension testing device according to an embodiment of the present invention.

Referring to FIG. 2 and FIG. 5a, FIG. 5a is a schematic view of the structure of the clamp 40 shown in FIG. 2 according to an embodiment of the present invention. As shown in FIG. 5a, the clamp 40 comprises a bottom member 402, two jaws 404 (or at least two jaws 404 as needed) disposed at the bottom member 402, and two bolts 406 (or at least two bolts 406 as needed) for passing through said two jaws 404. The pin 104 is clamped by and between said two jaws 404. The bolts 406 hold said two jaws 404 firmly to clamp the pin 104 between said two jaws 404 tightly. The clamping surfaces of said two jaws 404 have serrate embossment, stripe embossment, lattice embossment, or irregular embossment, so as to provide friction required for clamping the pin 104. Two screw holes 408 which can be engaged with the bolts 406, respectively, are disposed at said two jaws 404. With the bolts 406 being screwed to the screw holes 408, respectively, said two jaws 404 can clench the pin 104 tightly. The bolts 406 each have a handle, a knob, or a head, and come in the form of butterfly bolts, thumb bolts, or plastic head bolts as needed.

The tension test performed on the electronic element 100 by means of the tension testing device 2 involves: resting the body 102 on the seating portion 302 of the hanger 30 in a manner that the pin 104 passes through the opening 306; clamping the pin 104 with said two jaws 404 of the clamp 40, wherein the bolts 406 press said two jaws 404 toward each other tightly to clench the pin 104 between said two jaws 404 tightly; starting the tensiometer 20 and progressing and recording the tension test; and loosening, upon completion of the tension test, said two jaws 404 by the bolts 406 to take out the electronic element 100. The pin 104 of the clamp 40 is vertical while the body 102 rests on the hanger 30. The tension is applied in a direction parallel to the pin 104. The included angle of the L-shaped hanger 30 per se is a right angle, and thus there is no force component between the body 102 and the pin 104. Even if the included angle of the L-shaped hanger 30 per se is not a right angle because of a manufacturing tolerance, the tension test can be preceded by a pre-test procedure that involves measuring the hanger 30, calibrating the measurements, and calculating a force component, so as to analyze the tension test result accurately.

Figure 4B:
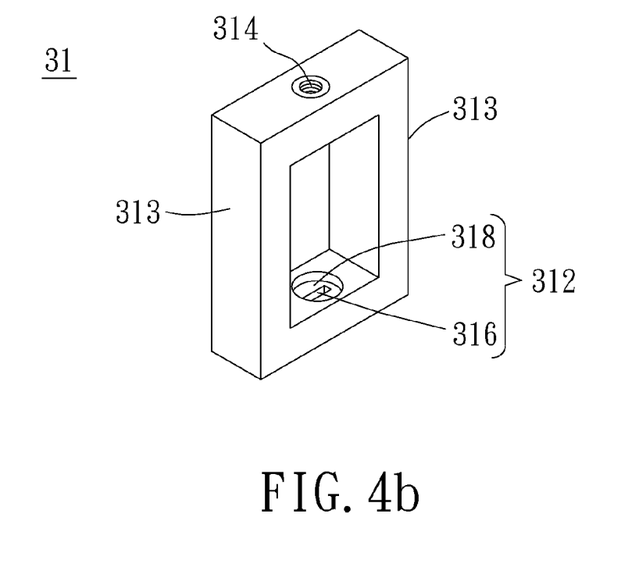
Figure 4C:
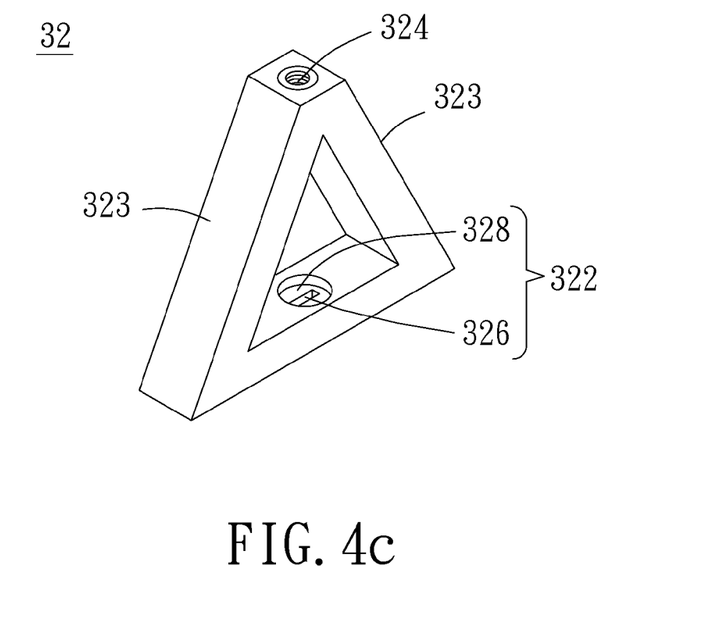
Figure 4D:
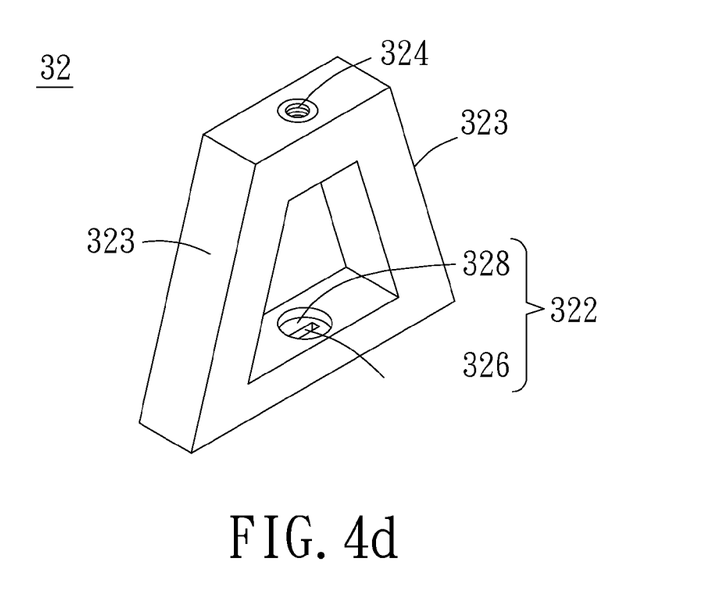

Referring to FIG. 4b, FIG. 4c and FIG. 4d, there are shown schematic views of the structure of a hanger of the tension testing device according to an embodiment of the present invention. A hanger is of a frame structure with bilateral symmetry according to an embodiment of the present invention; referring to FIG. 4b, a hanger 31 is of a rectangular frame structure. A seating portion 312 is centrally disposed at the bottom side of the hanger 31 for underpinning the body 102. The seating portion 312 comprises an opening 316 through which the pin 104 passes to penetrate the seating portion 312. The seating portion 312 further comprises a receiving recess 318 corresponding in shape to the bottom of the body 102, and having a rim which encircles the upper periphery of the opening 316, such that the receiving recess 318 is capable of receiving the body 102 and conducive to the passage of the pin 104 through the opening 316 with a view to enabling the hanger 31 to underpin the body 102 and projecting the pin 104 in the direction of the base 10. A jointing portion 314 is centrally disposed at the top side of the hanger 31 and coupled to the pulling portion 202. The jointing portion 314 is a screw hole, a ring, or a hook. The pulling portion 202 is implemented in the form of a bolt, a ring, or a hook, respectively. With the hanger 31 being of the aforesaid rectangular frame structure, the applied tension is conveyed along said two lateral sides 313 vertically, hence, no force component develops between the body 102 and the pin 104.

Furthermore, referring to FIG. 4c and FIG. 4d, there are shown schematic views of the structure of a hanger of the tension testing device according to an embodiment of the present invention. As shown in FIG. 4c, a hanger 32 is of an equilateral triangle-shaped frame structure which has three sides of equal length, namely two lateral sides 323 and a bottom side. Alternatively, as shown in FIG. 4d, the hanger 32 is of an isosceles trapezoidal frame structure which has four sides, namely a top side, a bottom side parallel to the top side, and two lateral sides 323. A seating portion 322 is centrally disposed at the bottom side for receiving the body 102. The seating portion 322 comprises an opening 326 through which the pin 104 passes to penetrate the seating portion 322. The seating portion 322 further comprises a receiving recess 328 corresponding in shape to the bottom of the body 102, and having a rim which encircles the upper periphery of the opening 326, such that the receiving recess 328 is capable of receiving the body 102 and conducive to the passage of the pin 104 through the opening 326 with a view to enabling the hanger 31 to underpin the body 102 and projecting the pin 104 in the direction of the base 10. Referring to FIG. 4c and FIG. 4d, a jointing portion 324 is centrally disposed at the top vertex and the top side of the hanger 32, respectively, and coupled to the pulling portion 202. The jointing portion 324 is a screw hole, a ring, or a hook. The pulling portion 202 is implemented in the form of a bolt, a ring, or a hook. The applied tension is conveyed along said two lateral sides 323, due to the bilateral symmetry of the hanger 32. Therefore, non-vertical force components offset each other. Accordingly, the applied tension is always conveyed vertically, and no component force develops between the body 102 and the pin 104.

Figure 5B:
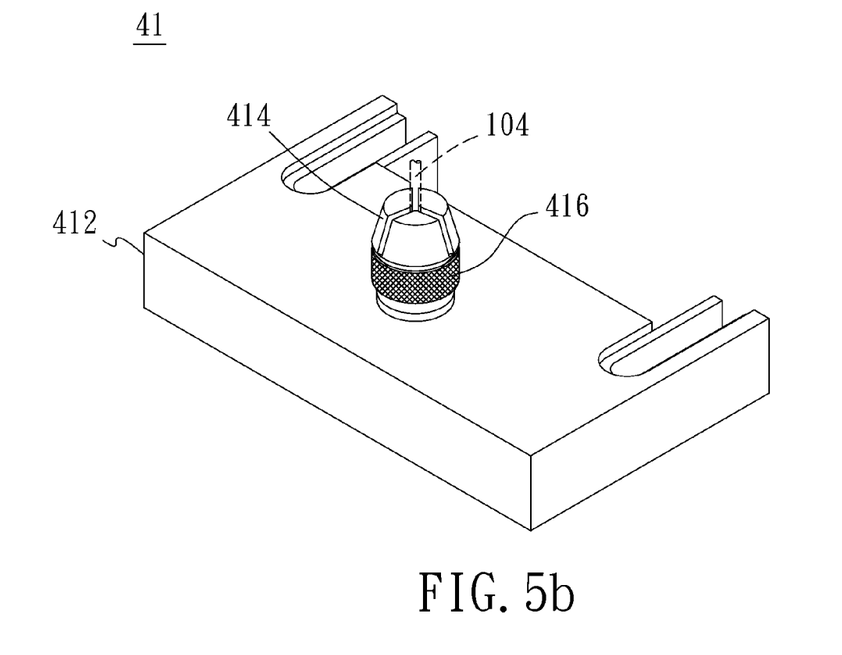

Referring to FIG. 5b, there is shown a schematic view of the structure of a clamp 41 of the tension testing device according to an embodiment of the present invention. As shown in FIG. 5b, the clamp 41 comprises a bottom member 412, a clamping head 414 disposed on the bottom member 412, and a sleeve 416 disposed around the clamping head 414. The sleeve 416 holds the clamping head 414 tightly so as to clamp the pin 104 therein. The sleeve 416 has an engaging structure or a screwing structure, such that the clamping head 414 clamps the pin 104 therein tightly. The clamping head 414 comprises a plurality of claws for holding the pin 104 tightly when the sleeve 416 draws the claws closer to each other.

Unlike a conventional tension testing device, the tension testing device of the present invention simplifies a testing procedure, enhances ease of use, shortens the required duration of a tension test, and enhances the efficiency of the tension test. A pin strength tension test conducted on an electronic element by the tension testing device of the present invention has the following advantages: preventing the body from being clamped to deformation or bad alignment; dispensing a welding and unwelding process which must otherwise be performed on a pin and a test lead to the detriment of the appearance of the electronic element according to the prior art; with a hanger and a clamp working together, the development of a force component derived from an applied tension is precluded, thereby providing a stable test process and yielding a reliable test result. Accordingly, the tension testing device of the present invention features ease of use, a stable test process, and reliable test results, and is effective in enhancing production efficiency and product quality.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A tension testing device for use with a tension test for evaluating a bonding strength between a body and a pin of an electronic element, the tension testing device comprising:
   a base provided thereon with a supporting member and provided with a carrying member disposed at the supporting member;
   a tensiometer carried by the carrying member and having a pulling portion;
   a hanger coupled to the pulling portion for underpinning the body and projecting the pin in the direction of the base; and
   a clamp disposed on the base and positioned beside the hanger, for clamping the pin.

2. The tension testing device of claim 1, wherein the carrying member comprises an adjusting mechanism for adjusting a position of the carrying member relative to the supporting member.

3. The tension testing device of claim 1, wherein the pulling portion is at least one of a bolt, a ring, and a hook.

4. The tension testing device of claim 1, wherein the hanger is one of an L-shaped structure and a frame structure with bilateral symmetry.

5. The tension testing device of claim 4, wherein the hanger further comprises a jointing portion and a seating portion having an opening, and the seating portion is used for underpinning the body, and the pin passes through the opening to penetrate the seating portion.

6. The tension testing device of claim 5, wherein the jointing portion is at least one of a screw hole, a ring, and a hook, for coupling to the pulling portion.

7. The tension testing device of claim 5, wherein the seating portion comprises a receiving recess having a rim encircling an upper periphery of the opening.

8. The tension testing device of claim 1, wherein the clamp comprises a bottom member, a plurality of jaws disposed at the bottom member, and a plurality of bolts for passing through the jaws and holding the jaws firmly to clamp the pin there between tightly.

9. The tension testing device of claim 8, wherein clamping surfaces of the jaws have at least one of serrate embossment, stripe embossment, lattice embossment, and irregular embossment.

10. The tension testing device of claim 1, wherein the clamp comprises a bottom member, a clamping head disposed on the bottom member, and a sleeve disposed around the clamping head, the sleeve holding the clamping head tightly so as to clamp the pin therein.

* * * * *